United States Patent
Mueller et al.

(10) Patent No.: US 7,742,799 B2
(45) Date of Patent: Jun. 22, 2010

(54) CATHETER TIP TRACKING FOR INTERVENTIONAL PROCEDURES MONITORED BY MAGNETIC RESONANCE IMAGING

(75) Inventors: Joerg C. Mueller, Buchholz (DE); Steffen Weiss, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1143 days.

(21) Appl. No.: 10/570,711

(22) PCT Filed: Sep. 1, 2004

(86) PCT No.: PCT/IB2004/051660

§ 371 (c)(1),
(2), (4) Date: Mar. 3, 2006

(87) PCT Pub. No.: WO2005/024447

PCT Pub. Date: Mar. 17, 2005

(65) Prior Publication Data

US 2007/0043288 A1    Feb. 22, 2007

Related U.S. Application Data

(60) Provisional application No. 60/501,532, filed on Sep. 9, 2003.

(51) Int. Cl.
*A61B 5/055*    (2006.01)
(52) U.S. Cl. ............... 600/410; 600/407; 600/411; 600/423; 600/424; 324/304; 324/318; 324/322
(58) Field of Classification Search .............. 600/410, 600/411, 423, 424; 324/307, 309, 318, 322
See application file for complete search history.

(56) References Cited

U.S. PATENT DOCUMENTS

| | | | | |
|---|---|---|---|---|
| 5,876,338 A * | 3/1999 | Gilderdale et al. | ......... | 600/411 |
| 6,236,205 B1 * | 5/2001 | Ludeke et al. | ......... | 324/318 |
| 6,280,385 B1 * | 8/2001 | Melzer et al. | ......... | 600/423 |
| 6,332,089 B1 * | 12/2001 | Acker et al. | ......... | 600/424 |
| 6,512,941 B1 | 1/2003 | Weiss et al. | ......... | 600/410 |
| 6,537,232 B1 * | 3/2003 | Kucharczyk et al. | ....... | 600/561 |
| 6,909,818 B2 * | 6/2005 | Tsushima et al. | ......... | 385/14 |
| 6,925,322 B2 * | 8/2005 | Helfer et al. | ......... | 600/423 |
| 6,980,848 B2 * | 12/2005 | Helfer et al. | ......... | 600/423 |
| 7,048,716 B1 * | 5/2006 | Kucharczyk et al. | ... | 604/164.01 |

(Continued)

OTHER PUBLICATIONS

Ackerman, J.L., et al.; Rapid 3D Tracking of Small RF Coils; 1986; Proc. Of 5$^{th}$ SMRM; pp. 1131-1132.

(Continued)

*Primary Examiner*—Brian Casler
*Assistant Examiner*—Baisakhi Roy

(57) ABSTRACT

A tracking device (20, 20') for tracking a tip (14) of an interventional instrument such as a catheter (10) during an interventional procedure performed on an associated subject (12) and monitored by magnetic resonance imaging includes a resonant circuit (22) disposed at the tip (14) of the catheter (10). The resonant circuit (22) includes a coil (32, 32') having a coil inductance and a light-sensitive metal-insulator-semiconductor capacitor (30) optically coupled with an optical fiber (36) and having a selected capacitance determined by an intensity of light delivered by the optical fiber (36). A selected resonance frequency of the resonant circuit (22) is determined by the coil inductance and the selected capacitance. The resonance frequency is adjusted by modulating the intensity of light delivered to the light-sensitive metal-insulator-semiconductor capacitor (30).

20 Claims, 8 Drawing Sheets

U.S. PATENT DOCUMENTS

| | | | |
|---|---|---|---|
| 7,162,293 B2 * | 1/2007 | Weiss | 600/411 |
| 7,389,137 B2 * | 6/2008 | Helfer et al. | 600/423 |
| 7,440,792 B2 * | 10/2008 | Eggers | 600/410 |
| 7,479,157 B2 * | 1/2009 | Weber et al. | 623/1.15 |
| 2002/0013525 A1 | 1/2002 | Scott | 600/410 |
| 2003/0073898 A1 | 4/2003 | Weiss | 600/410 |
| 2003/0088181 A1 | 5/2003 | Gleich | 600/434 |
| 2004/0124838 A1 | 7/2004 | Duerk et al. | 324/304 |
| 2008/0157762 A1 * | 7/2008 | Weiss | 324/304 |

OTHER PUBLICATIONS

Bakker, C.J., et al.; Visualization of dedicated catheters using fast scanning techniques with Potential for MR-guided vascular interventions; 1996; MRM; 36:816-820.

Bartels, L.W., et al.; Endovascular interventional magnetic resonance imaging; 2003; Phys. Med. Biol.; 48:R37-R64.

Eggers, H., et al.; Image-Based Tracking of Optically Detunable Parallel Resonant Circuits; 2003; MRM; 49:1163-1174.

Glowinski, A., et al.; Catheter Visualization Using Locally Induces, Actively Controlled Field Inhomogeneities; 1997; MRM; 38:253-258.

Konings, M.K., et al.; Heating Around Intravascular Guidewires by Resonating RF Waves; 2000; J. of MRI; 12:79-85.

Ladd, M.E., et al.; Reduction of Resonant RF Heating in Intravascular Catheters Using Coaxial Chokes; 2000; MRM; 43:615-619.

Liu, C-Y., et al.; Safety of MRI-Guided Endovascular Guidewire Applications; 2000; J. of MRI; 12:75-78.

Maier, S.E., et al.; Safety of MR Tracking Catheters; 1995; Proc. Of the SMR/ESMRMB Joint Meeting; p. 473.

McKinnon, G.C., et al.; Towards Active Guidewire Visualization in Interventional Magnetic Resonance Imaging; Mar. 1996; MAGMA; abstract.

Sze, S.M.; "Physics of Semiconductor Devices"; John Wiley & Sons, $2^{nd}$ ed.1981; Chapter 7—MIS Diode and Charge-Coupled Device; pp. 362-379.

Uelzen, T.; Development of a fast localizable patient-safe MR-Catheter for MR-guided Intravascular interventions based on Micro Systems Technology (LOMKAT).

Unal, O., et al.; A rapid 2D time-resolved variable-rate k-space sampling MR technique for Passive Catheter Tracking during endovascular procedures; 1998; MRM; 40:356-362.

Weiss, S., et al.; MR-controlled fast optical switching of a resonant circuit mounted to the tip Of a clinical catheter; 2001; Proc. Intl. Soc. Mag. Reson. Med.; 9:544.

Wong, E.Y., et al.; An optical system for wireless detuning of parallel resonant circuits; 2000; J. of MRI; 12:632-638.

* cited by examiner

CATHETER TIP TRACKING FOR INTERVENTIONAL PROCEDURES MONITORED BY MAGNETIC RESONANCE IMAGING

CROSS REFERENCE TO RELATED APPLICATIONS

This application claims the benefit of U.S. provisional application Ser. No. 60/501,532 filed Sep. 9, 2003, which is incorporated herein by reference.

DESCRIPTION

The following relates to the interventional medical arts. It finds particular application in catheter tracking for interventional procedures in conjunction with magnetic resonance imaging, and will be described with particular reference thereto. However, it also finds application in monitoring other types of interventional procedures in a magnetic resonance environment.

During interventional procedures monitored by magnetic resonance imaging, a catheter or other interventional instrument is inserted into a subject and manipulated to perform one or more selected interventional tasks. Examples of such interventional procedures include biopsy, fluid injection, physiological monitoring, balloon angioplasty, radio frequency catheter ablation, insertion of a temporary cardiac pacemaker, or the like. During the interventional procedure, the subject is imaged by a magnetic resonance imaging scanner at least within the interventional region. Advantageously, these procedures are minimally invasive, typically involving insertion of a catheter into a vein, an artery, a bladder duct, or another fluid conduit within the subject However, the catheter or other instrument is typically not directly imaged by the magnetic resonance imaging scanner. To provide guidance for manipulating the catheter inside of the subject, a tracking mechanism is needed. The tip tracking mechanism preferably operates in conjunction with the magnetic resonance imaging so that a position of the catheter tip is indicated in or superimposed on the reconstructed magnetic resonance images or so that the co-ordinates of the catheter tip are measured in order to set position of the slice being imaged automatically to contain the catheter tip.

In one catheter tip tracking approach, a small radio frequency antenna coil is arranged on the tip of the catheter and is used as a miniature receive coil. It is typically connected to one of the receivers of the magnetic resonance imaging scanner by wires running inside of or alongside the catheter. The received antenna signal is processed to determine position coordinates of the catheter tip. The position can be determined by just acquiring three orthogonal projections of the subject, which is much faster than acquiring a complete image. Therefore, the position determination can be interleaved with the imaging process without causing noticeably delay. However, this approach has the disadvantage that the radio frequency excitation pulses transmitted by the scanner for magnetic resonance imaging couple to the wires and can generate high electrical fields which can cause heat in the subject In another tracking approach, a material that causes magnetic susceptibility variation is disposed on or inside of the catheter tip. This approach typically provides weak contrast in the reconstructed images, making tip tracking difficult. Stronger contrast can be achieved by using a material having more pronounced magnetic susceptibility characteristics; however, such pronounced magnetic susceptibility variation causes distortion or attenuation of the reconstructed images precisely in the area where the interventional procedure is being performed. Moreover, there is no way to "turn off" the catheter tip contrast once the catheter tip is positioned appropriately for performing the procedure. Still further, this approach does not provide co-ordinates of the catheter tip for setting the imaging slice automatically to contain the catheter tip.

In yet another catheter tip tracking approach, a resonant circuit including a photodiode is disposed at the tip of the catheter. The resonance frequency of the resonant circuit is changed between the magnetic resonance frequency and a significantly shifted frequency by illuminating or not illuminating the photodiode. The switching light is applied to the photodiode through an optical fiber running inside of or alongside the catheter. When the resonant circuit is tuned to the magnetic resonance frequency it resonates responsive to radio frequency excitation of the magnetic resonance signal. In that case the MR signal is amplified locally generating a hot spot in the image (MR visible state). The signal amplification can also be used to determine the co-ordinates of the catheter tip in projection measurements. As a further advantage, once the catheter tip is in position for performing the interventional procedure or when a high resolution image is to be generated to check tip position, the light intensity is switched to detune the resonant circuit away from the resonant condition so that the resonant circuit becomes substantially invisible in the reconstructed image.

This approach also has certain disadvantages. The resonant circuit is fairly large, generally including at least the photodiode, a microcoil inductor, and at least two capacitors: one to provide a resonant circuit with in conjunction with the microcoil inductor; and a second capacitor to block d.c. current flowing through the photodiode. The photodiode has an impedance with a substantial conductance component, which limits the quality factor of the resonant circuit. A reduced quality factor reduces contrast of the catheter tip in the reconstructed image, and also implies a larger shift in resonance frequency is needed to detune the resonant circuit to substantial invisibility.

The quality factor typically reduces to close to unity during illumination due to resistive losses in the photodiode. As a result, the tuned resonance frequency preferably corresponds to the unilluminated condition to provide a high quality factor in the MR visible state. To tune the resonance circuit to the MR resonance frequency in the unilluminated state, the circuit must be precisely manufactured to the selected resonance frequency. If the tuned resonance frequency is obtained by illumination, for example, to account for tolerances of the parts of the resonant circuit, for detuning due to changes of the electrical surrounding of the circuit or for a different magnetic field applied by the magnetic resonance imaging scanner, then the quality factor is greatly reduced.

Still further, while the resonant circuit can be switched between the visible state and the invisible state by light intensity modulation, the photodiode is operating in an unbiased state and has a relatively slow response time. Thus, switching time between the visible and invisible states is limited to about 0.1 millisecond or longer. One application of resonant circuit visibility switching is removal of background magnetic resonance signals from the imaging subject during tip tracking. In this application, magnetic resonance imaging data are automatically acquired with the resonant circuit alternating between the visible and invisible states, and the reconstructed images or projections in the visible and invisible states are subtractively combined to substantially remove the background image signal. Because the switching time is limited to about 0.1 milliseconds or longer, this automatic tracking is susceptible to blurring due to motion of the subject or to changes of the state of the magnetization in the subject.

The present invention contemplates an improved apparatus and method that overcomes the aforementioned limitations and others.

According to one aspect, an interventional instrument is disclosed for use in an interventional procedure performed on an associated subject and monitored by magnetic resonance imaging. An element is adapted for insertion into the associated subject for performing the interventional procedure. An optical fiber is arranged to deliver light to a selected location on the element. A resonant circuit is disposed at the selected position on the element. The resonant circuit includes a coil having a coil inductance and a light-sensitive metal-insulator-semiconductor capacitor optically coupled with the optical fiber and having a selectable capacitance determined by an intensity of light delivered thereto by the optical fiber. A selected resonance frequency of the resonant circuit is determined by the coil inductance and the selected capacitance. The selected resonance frequency is selectable by adjusting the light intensity to correspond to a tuned resonance frequency detected by the magnetic resonance imaging.

According to another aspect, a system is disclosed for performing an interventional procedure on an associated subject monitored by magnetic resonance imaging. The system includes a magnetic resonance imaging scanner for performing the magnetic resonance imaging, and the interventional instrument as set forth in the previous paragraph.

According to yet another aspect, a method of using the interventional instrument including the resonant circuit as set forth above is provided. Magnetic resonance is excited in a three-dimensional volume containing the selected location on the element. Spatially selective projection data is acquired along a projection direction. During the acquiring of each spatial position along the projection direction, the intensity of light delivered to the light-sensitive metal-insulator-semiconductor capacitor is intensity-modulated to modulate the selected resonance frequency between the tuned resonance frequency and a detuned resonance frequency not detected by the magnetic resonance imaging. For each spatial position along the projection direction, projection data acquired with the selected resonance frequency at the tuned resonance frequency and projection data acquired with the selected resonance frequency at the detuned resonance frequency is subtractively combined to produce subtractively combined projection data.

One advantage resides in providing a catheter tip tracking device having reduced size.

Another advantage resides in providing a catheter tip tracking device including a resonant circuit with a high quality factor.

Another advantage resides in providing a catheter tip tracking device having a tuned resonance frequency that is adjustable by control of light intensity applied thereto.

Still yet another advantage resides in providing a catheter tip tracking device having a rapid switching response.

Still yet another advantage resides in providing a method for tracking a catheter tip using said catheter tip tracking device with rapid switching response, the tracking method having reduced sensitivity to subject motion or other sources of differences in the data to be subtracted as changes in the state of the magnetization.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a system for performing interventional applications using a catheter with a tip tracking device monitored by a magnetic resonance imaging scanner.

Figure 5:
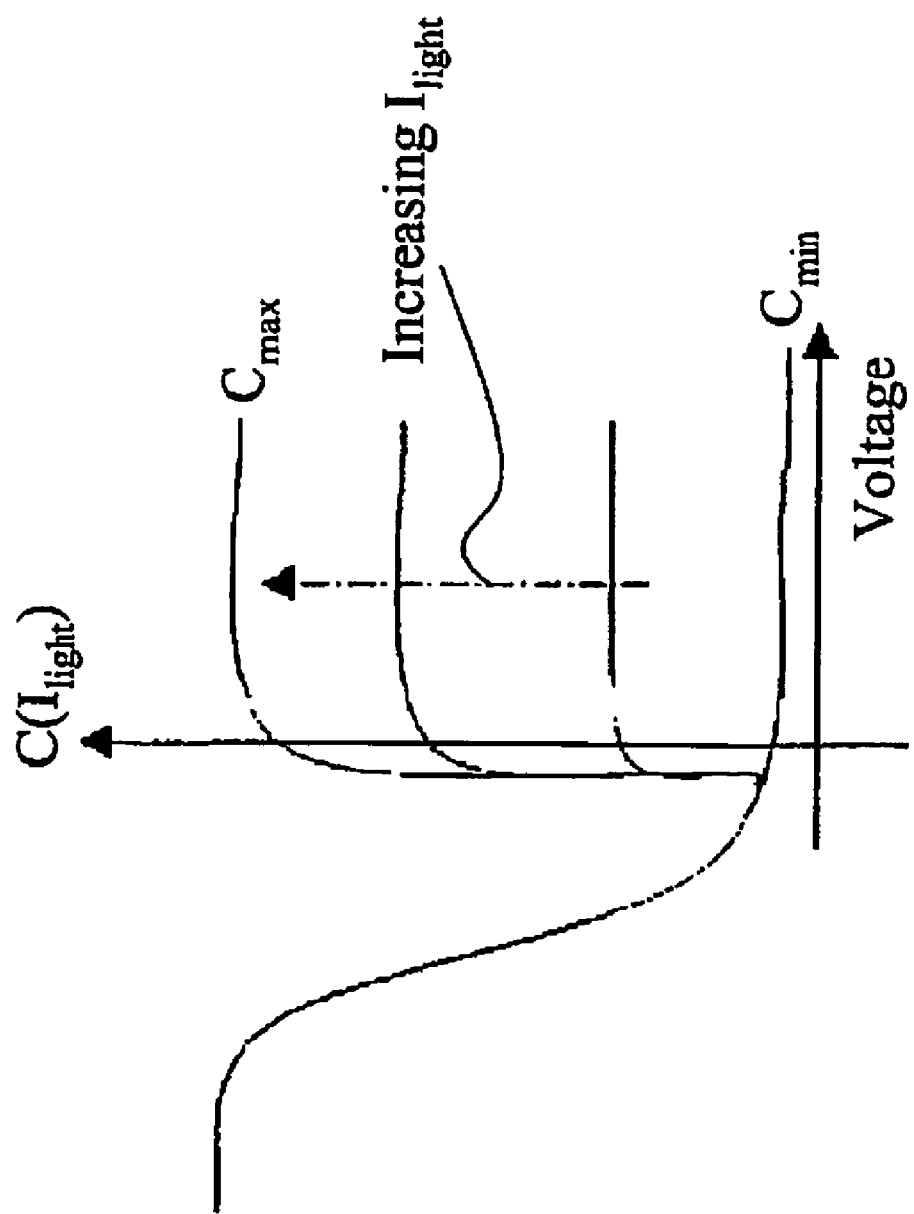
Figure 6:
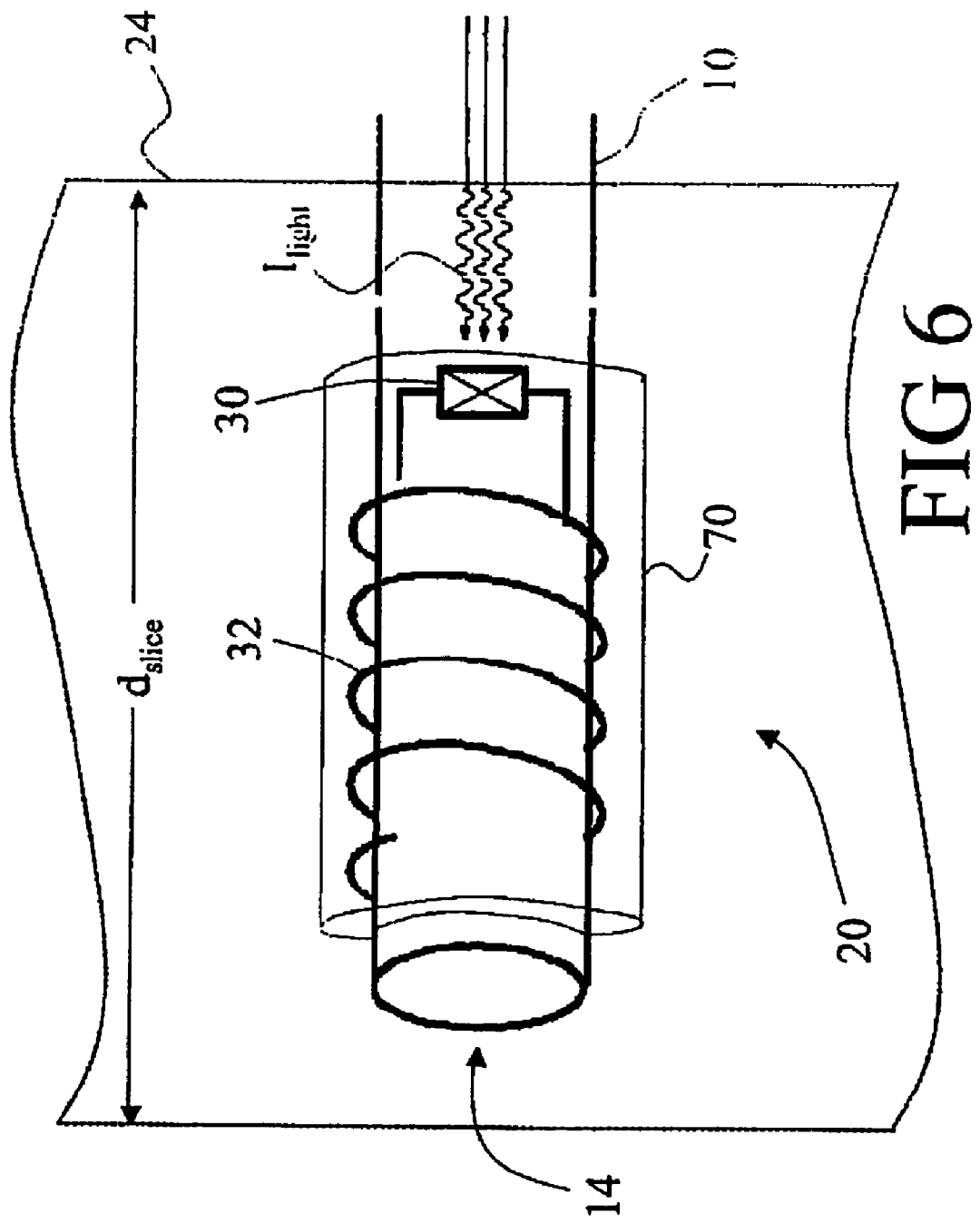

FIG. 5 diagrammatically shows a capacitance-voltage-light characteristic of the light sensitive metal-insulator-semiconductor capacitor component of the tip tracking device FIG. 6 diagrammatically shows one embodiment of the tip tracking device.

Figure 7:
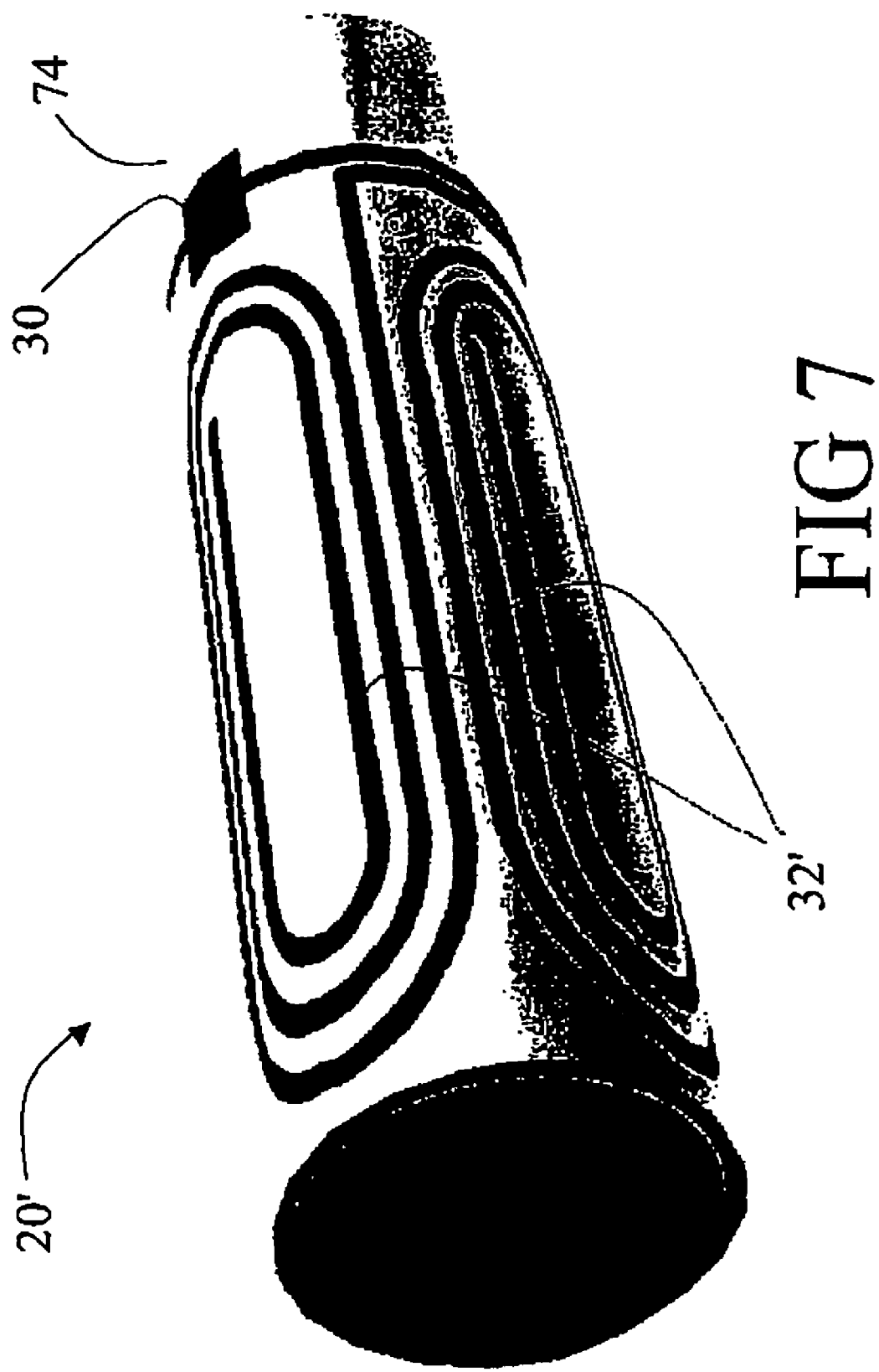

FIG. 7 shows a perspective view of a preferred embodiment of the tip tracking device.

Figure 8:
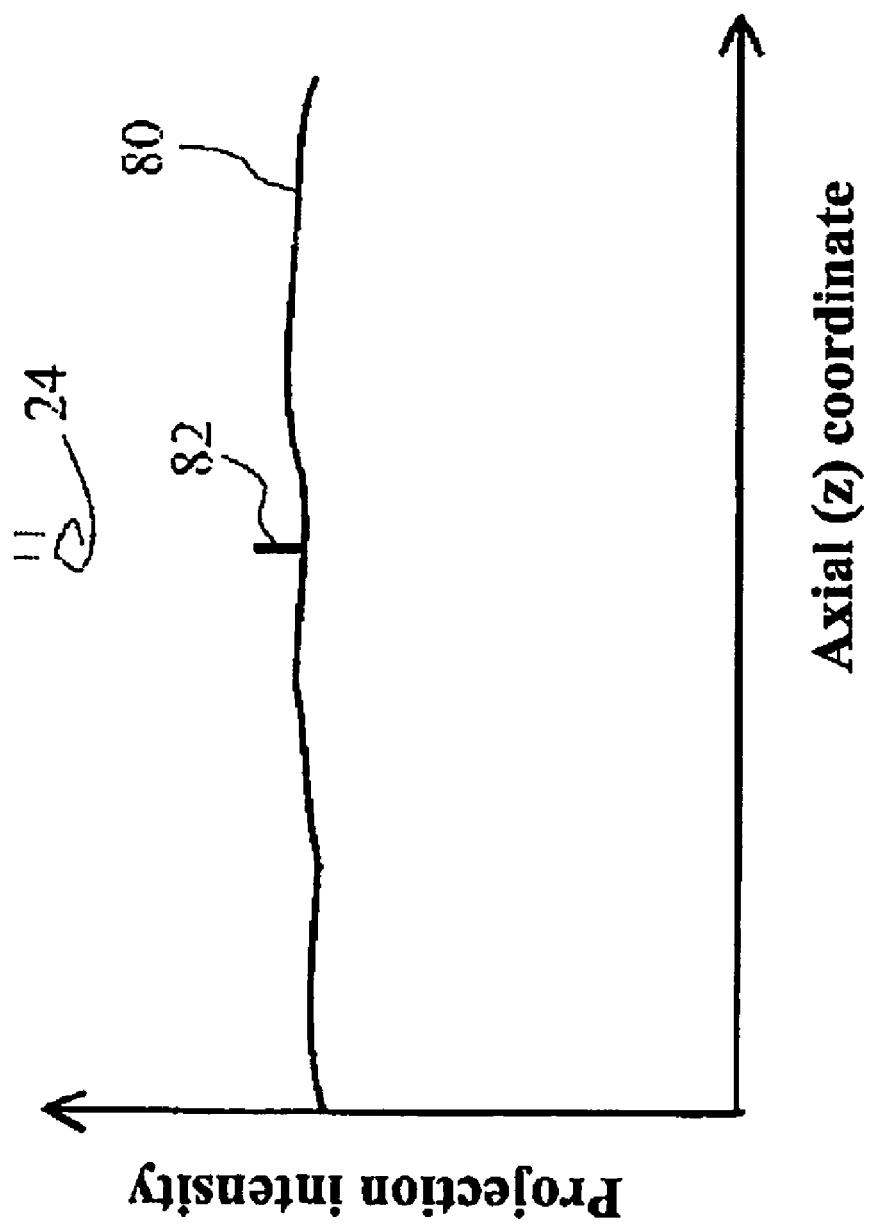

FIG. 8 diagrammatically plots magnetic resonance projection data taken along the z-direction perpendicular to imaging slices.

Figure 1:
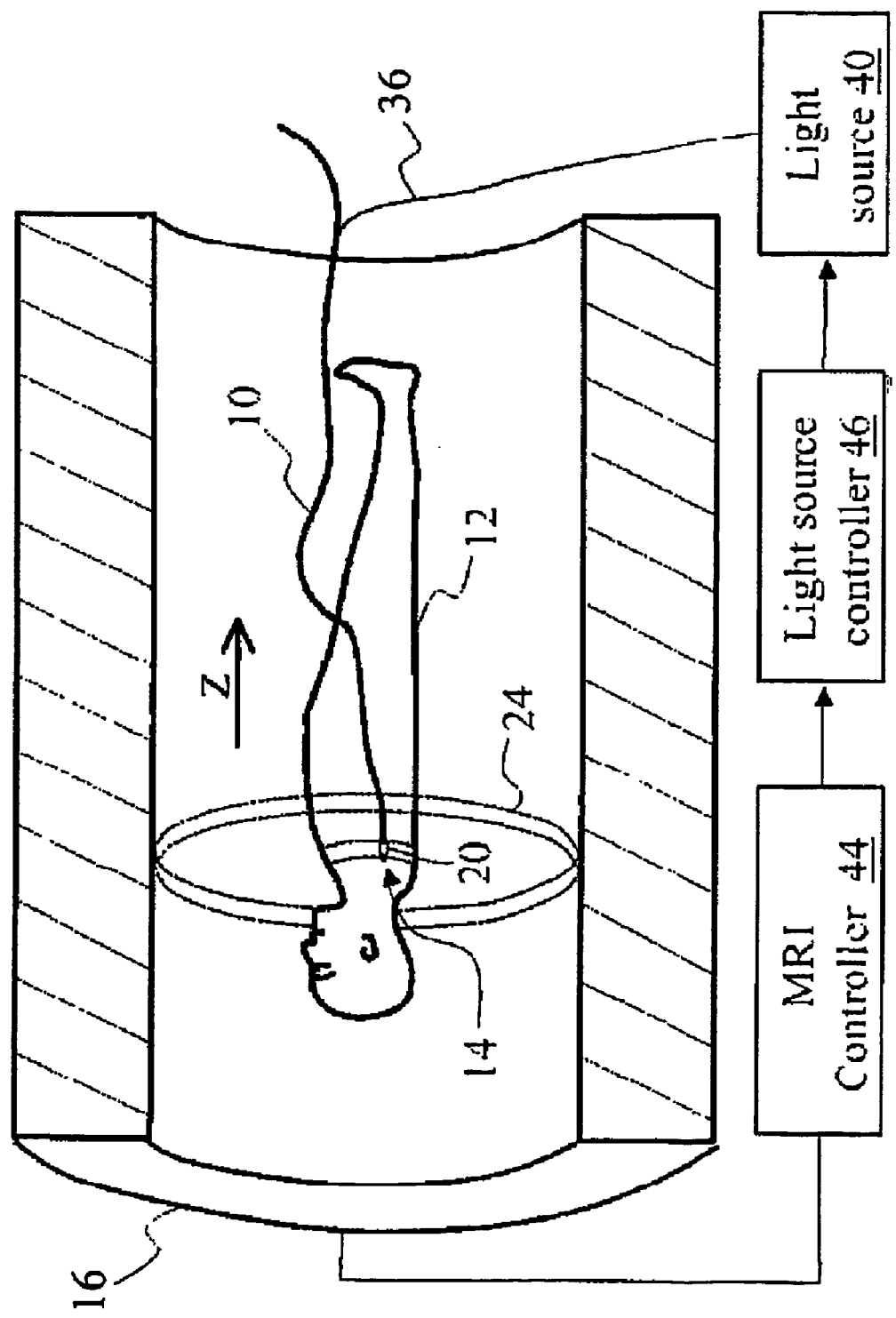

With reference to FIG. 1, a system for performing an interventional procedure includes an interventional instrument, such as a catheter 10, that is inserted into an associated subject 12. A position of a tip 14 of the catheter 10 is monitored using a magnetic resonance imaging scanner 16 that images a tip tracking device 20 disposed at the tip 14 of the catheter 10. The catheter 10 is often a flexible tubular element, and can have zero, one, or more lumens serving as fluid transport pathways or conduits for optical fibers, electrical wires, or the like. The catheter 10 may be a single-piece flexible tubular element, or it may be comprised of a plurality of tubular sub-elements having joined ends. In the latter arrangement, a total length of the catheter is determined by a number of the joined tubular sub-elements. Rigid interventional instruments are also contemplated.

The catheter 10 can be substantially any type of catheter, such as an arterial line, a venous line, a central line, a cardiac catheter, a bladder catheter, or the like. Typical interventional procedures performed using catheters include biopsy, fluid injection, physiological monitoring, balloon angioplasty, radio frequency catheter ablation, insertion of a temporary cardiac pacemaker, or the like. The tip tracking device 20 is readily adapted for substantially any type of interventional instrument and can be employed in substantially any type of interventional procedure. The tip tracking device 20 is disposed at the tip 14 of the catheter 10, that is, typically within a few millimeters of the tip 14.

The magnetic resonance imaging scanner 16 includes various components for exciting and spatially encoding magnetic resonance in at least a selected portion of the imaging subject 12 for receiving magnetic resonance signals from the subject, and for computing a reconstructed image based on the received magnetic resonance signals. In FIG. 1 the magnetic resonance imaging scanner 16 is diagrammatically represented by illustrating a perspective sectional view of the main magnet assembly of the magnetic resonance imaging scanner 16, which defines a generally cylindrical magnet bore of the magnetic resonance imaging scanner 16. Those skilled in the art recognize that the main magnet assembly includes various components not shown in FIG. 1, typically including: main magnet coils for generating a substantially uniform longitudinal magnetic field aligned parallel to a cylinder axis of a magnet bore (that is, parallel or anti-parallel to a z-direction indicated in FIG. 1); magnetic field gradient coils for producing magnetic field gradients in three-dimensional space within the magnet bore; one or more radio frequency coils for generating or detecting magnetic resonances; and so forth. The main magnet coils are preferably superconducting coils, although resistive coils or a fixed magnet can also be employed. Vertical field, open, and other magnet configurations are also contemplated.

In operation, the radio frequency coils generate magnetic resonances that are spatially encoded by magnetic field gradients produced by the magnetic field gradient coils. In one suitable imaging pulse sequence, a slice selective magnetic field gradient is applied along the longitudinal or z-direction during a radio frequency excitation pulse to restrict magnetic resonance excitation to a selected planar slice, such as exemplary planar slice 24 indicated in FIG. 1 which contains the tip tracking device 20. During magnetic resonance readout, phase encode magnetic field gradient pulses are applied in a phase encode direction perpendicular to the z-axis, and readout magnetic field gradients are applied in a readout direction perpendicular to the z-direction and perpendicular to the phase encode direction during magnetic resonance readout. The phase encode and readout gradients step the magnetic resonance readout through a two-dimensional k-space of the selected planar slice. The acquired magnetic resonance data are reconstructed using a two-dimensional Fourier transform processor to produce a reconstructed image of the slice 24. The pulse sequence is suitably repeated for successive spatially adjacent slices to generate a three-dimensional volume image.

The described magnetic resonance imaging scanner and the described operation thereof are exemplary only. Those skilled in the art can readily modify the described apparatus, imaging pulse sequence, and image reconstruction process for specific applications. Suitable imaging methods compatible with the tip tracking device 20 include substantially any type of magnetic resonance imaging method, such as echo planar imaging, imaging using sensitivity encoding, single-slice or multi-slice spin echo imaging, and so forth. It will be appreciated that both the tip tracking device 20 and surrounding areas of the imaging subject 12 are imaged, providing a context for the position of the tip 14 of the catheter 10.

Figure 2:
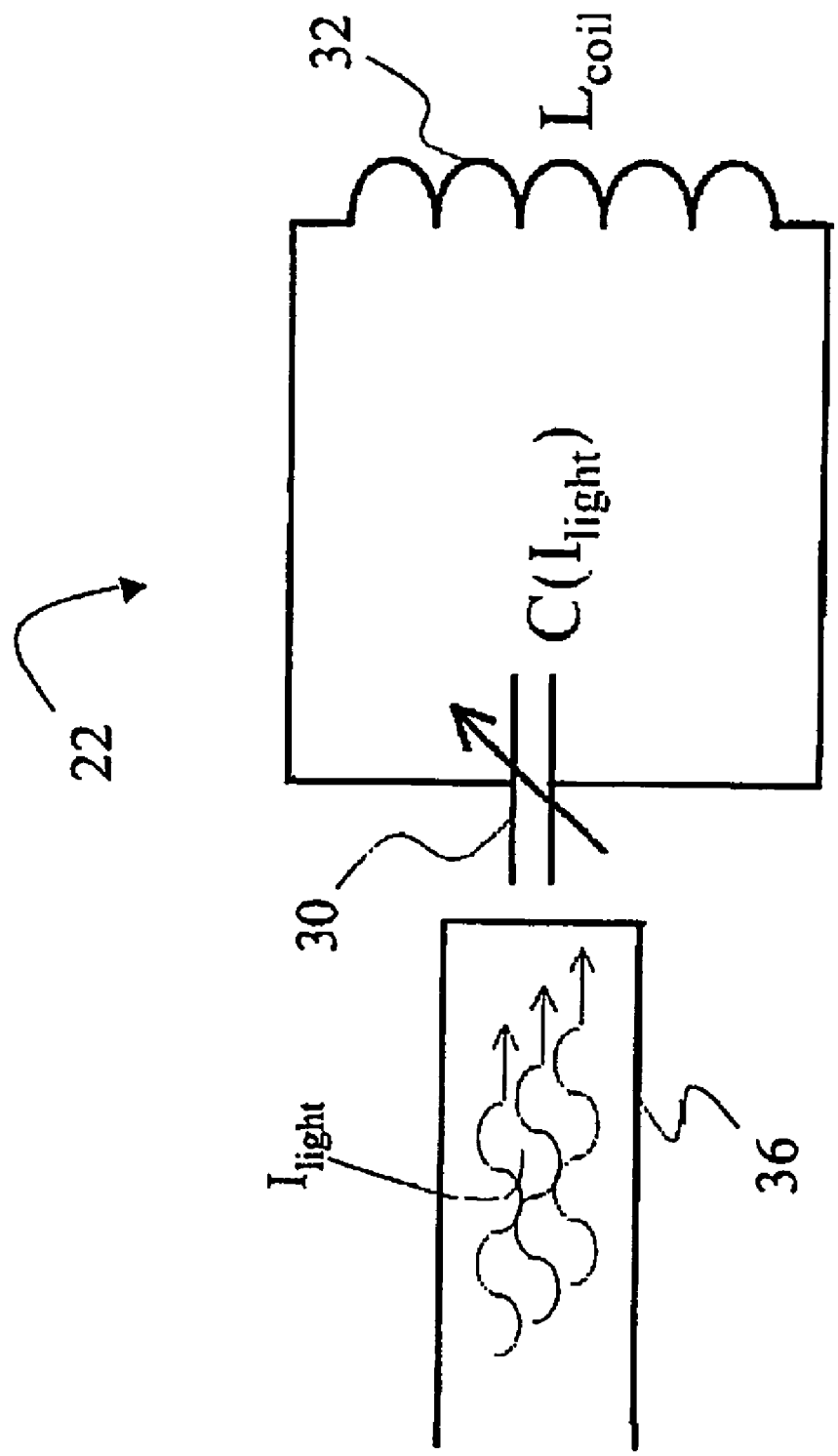
FIG. 2 shows the resonant circuit of the tip tracking device.

With continuing reference to FIG. 1 and with further reference to FIG. 2, The tip tracking device 20 includes a resonant circuit 22 (represented by an equivalent circuit diagram in FIG. 2) designed to have a selectable resonance frequency that is optically selected to correspond to a tuned resonance frequency of magnetic resonance excitation produced by the magnetic resonance imaging scanner 16. The resonant circuit 22 in the tuned state responds to the radio frequency excitation and produces a magnetic resonance response signal that is detected by the magnetic resonance imaging scanner 16 and imaged in the reconstructed image of the slice 24 containing the tip tracking device 20. The resonant circuit 22 includes a light sensitive metal-insulator-semiconductor capacitor 30 and an inductive coil 32 electrically connected together to define a resonant LC circuit. The coil 32 has an inductance $L_{coil}$ which is typically of order a few nanohenries.

The light sensitive metal-insulator-semiconductor capacitor 30 is optically coupled to an optical fiber 36 that delivers a selected intensity of light (denoted $I_{light}$) to the light sensitive metal-insulator-semiconductor capacitor 30. The optical fiber 30 is suitably disposed inside of a lumen of the catheter 10 or is suitably secured alongside the catheter 10 so that the optical fiber 36 is inserted into the subject 12 along with the catheter 10 as indicated in FIG. 1. The selected intensity of light is inputted to the optical fiber 36 by a light source 40 which is suitably a lamp, a light emitting diode, a laser, or the like. The light couples to the light sensitive metal-insulator-semiconductor capacitor 30 and determines a selected capacitance $C(I_{light})$ corresponding to the light intensity $I_{light}$. The inductance $L_{coil}$ and the selected capacitance $C(I_{light})$ determine the resonance frequency. For the resonant LC circuit of FIG. 2, the resonance frequency $f_{res}$ is given by:

$$f_{res} = \frac{1}{2\pi\sqrt{L_{coil} \cdot C(I_{light})}}. \qquad (1)$$

For other resonant circuits, such as for a resonant circuit including a plurality of inductive microcoils 32' (see for example FIG. 7 described infra) in place of the single coil 32, or for a plurality of circuits with several metal-insulator-semiconductor capacitors controllable by several corresponding optical fibers, a similar relationship between the resonant circuit components and the selected capacitance $C(I_{light})$ can be computed. As an example of applying Equation (1), for a proton gyrometric ratio $\gamma$=42 MHz/T and a magnetic field B=1.5T, the magnetic resonance frequency is $f_{mr}=\gamma B$ is about 63 MHz. For a coil inductance $L_{coil}$=150 nanohenries, the tuned resonance frequency $f_{res}$ corresponding to $f_{mr}$ is achieved for a selected capacitance computed from Equation (1) of $C(I_{light})$=42.5 picofarads.

With continuing reference to FIG. 1, the magnetic resonance imaging scanner 16 is controlled by a magnetic resonance imaging controller 44. When tip tracking is desired, the magnetic resonance imaging controller 44 controls a light source controller 46 to set the light intensity of the light source 40 to a value at which the selected capacitance $C(I_{light})$ tunes the resonant circuit 22 to the tuned resonance frequency. In this tuned state, the tip tracking device 20 is visible in the reconstructed image if the tip tracking device 20 resides within the slice or volume that is imaged. On the other hand, during imaging it may be desirable to remove the tip tracking device 20 from the image. In this case, the magnetic resonance imaging controller 44 controls the light source controller 46 to set the light intensity of the light source 40 to a value at which the selected capacitance $C(I_{light})$ detunes the resonant circuit 22 to a detuned resonance frequency. In this detuned state, the tip tracking device 20 is substantially invisible in the reconstructed image even if the tip tracking device 20 resides within the slice or volume that is imaged. The amount of detuning for substantial invisibility depends upon the quality factor of the resonant circuit 22.

Figure 3:
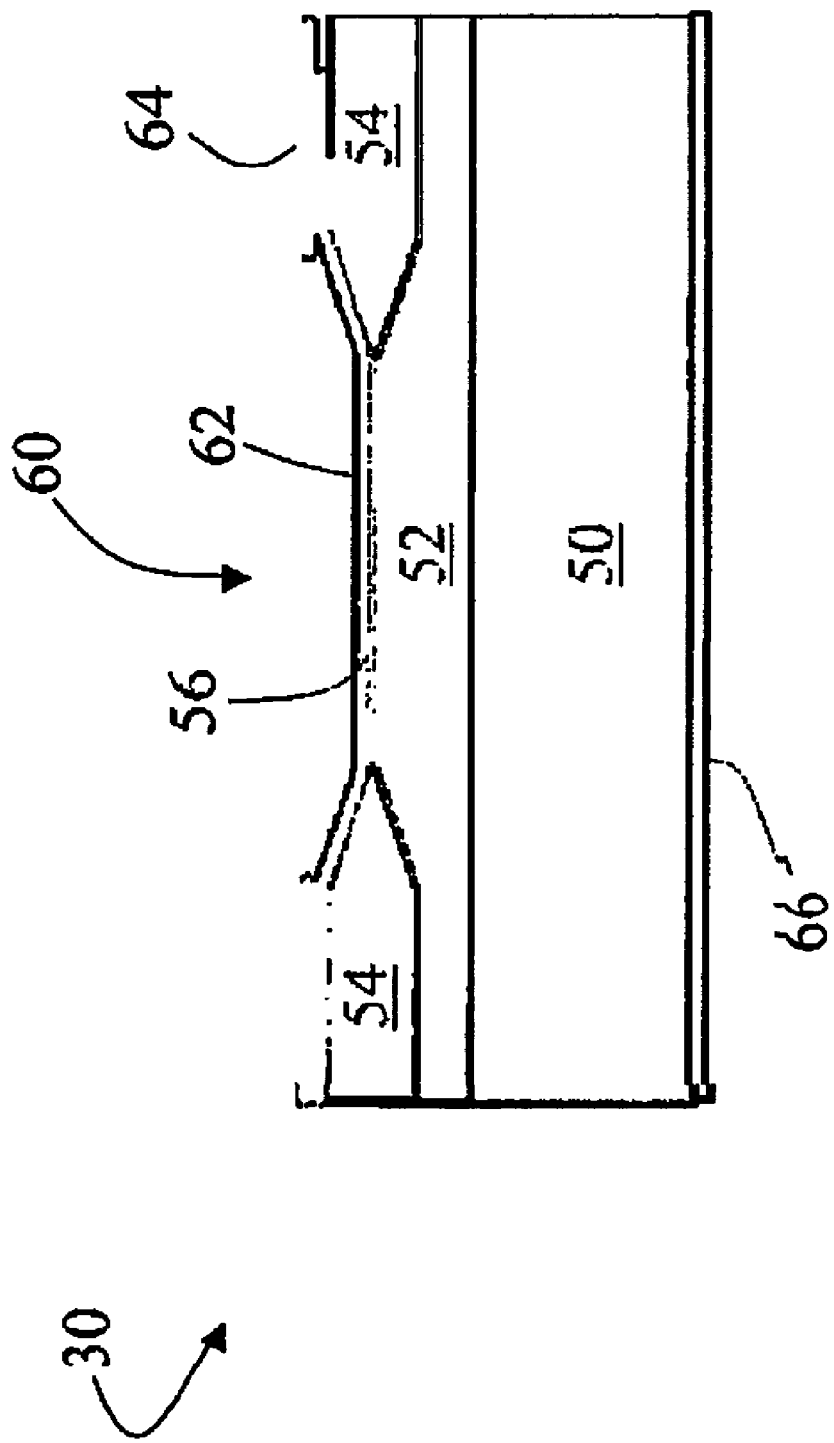
FIG. 3 shows a layer structure of a preferred light sensitive metal-insulator-semiconductor capacitor component of the tip tracking device.
Figure 4:
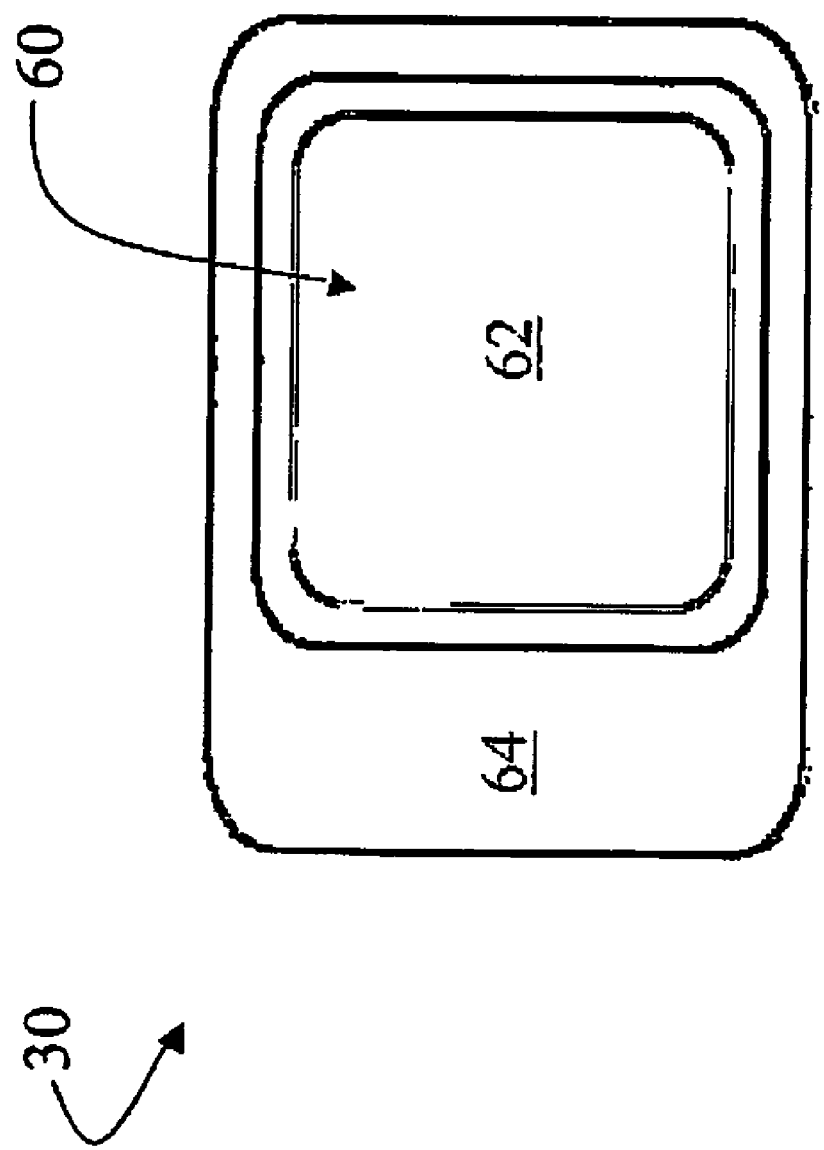
FIG. 4 shows a planar view of the preferred light sensitive metal-insulator-semiconductor capacitor component of FIG. 3.

With reference to FIGS. 3 and 4, a preferred embodiment of the light sensitive metal-insulator-semiconductor capacitor 30 includes a silicon metal-oxide-semiconductor (MOS) capacitor having a $p^+$ silicon substrate 50 and a more lightly doped p-type silicon layer 52 disposed over the substrate. The more lightly doped p-type silicon layer 52 is formed by epitaxial silicon deposition and has a doping concentration of preferably between about $10^{16}$ cm$^{-3}$ and about $10^{17}$ cm$^{-3}$, and more preferably about $5\times10^{16}$ cm$^{-3}$. The doping of the more lightly doped p-type silicon layer 52 can be introduced during the epitaxial growth or by subsequent processing, such as by ion implantation. The $p^+$/p silicon structure can be formed by other methods, such as by starting with a lightly doped substrate and forming the p$^+$/p doping structure by dopant diffusion or ion implantation of a suitable p-type dopant.

An insulator layer disposed over the more lightly doped p-type silicon layer 52 includes a thick field oxide 54, and a thinner aperture oxide 56 disposed in an area of an aperture 60 of the light sensitive metal-insulator-semiconductor capacitor 30. The oxide layers 54, 56 are suitably oxide layers formed by oxidation of selected portions of the lower doped p-type silicon layer 52. In another approach, the oxide layers 54, 56 are deposited by plasma deposition or another deposition technique. The thinner aperture oxide 56 preferably has a thickness between about 10 nm and about 20 nm, and more preferably has a thickness of about 17.5 nm. Lateral dimensions of the oxide layers 54, 56 are suitably defined by lithographic techniques.

A field electrode 62 extends over the device including over the aperture 60. The field electrode 62 is suitably a transparent thin conducting oxide such as an indium tin oxide layer. In another arrangement, the field electrode 62 is a polycrystalline silicon layer. In one embodiment, the field electrode 62 is a polycrystalline silicon layer preferably having a thickness of between 200 nm and 500 nm, and more preferably having a thickness of about 380 nm. The field electrode 62 should be sufficiently light-transmissive to permit a substantial portion of the light intensity $I_{light}$ to penetrate to the more lightly p-doped semiconductor layer 52. A contacting electrode 64 is disposed over the field electrode 62 in an area or areas outside of the aperture 60. The contacting electrode 64 together with a backside contacting electrode 66 disposed over a backside of the p$^+$ silicon substrate 50 provides electrical contact to the light sensitive metal-insulator-semiconductor capacitor 30. In a suitable embodiment, the contacting electrodes 64, 66 are suitably aluminum layers having thicknesses of about 1 micron.

A thickness of the more lightly doped p-type silicon layer 52 is preferably selected to substantially coincide with a depth of a space charge region in the more lightly doped p-type silicon layer 52 at zero potential. For a preferred p-type doping level of the lower doped p-type silicon layer 52 of about 5×10$^{16}$ cm$^{-3}$, the thickness of the more lightly doped p-type silicon layer 52 is preferably between about 200 nm and about 500 nm, and is more preferably about 300 nm. This thickness selection is designed to maximize a quality factor of the resonant circuit 22.

With continuing reference to FIGS. 3 and 4 and with further reference to FIG. 5, the light sensitive metal-insulator-semiconductor capacitor 30 has a capacitance $C(I_{light})$ versus voltage characteristic shown in FIG. 5. Under a dark condition (that is, without illumination, or in other words with illumination intensity $I_{light}$=0) a minimum capacitance $C_{min}$ labeled in FIG. 5 is obtained. With increasing illumination intensity $I_{light}$, the capacitance increases, up to a maximum value $C_{max}$. The absolute values of the minimum capacitance $C_{min}$ and the maximum capacitance $C_{max}$ include a dependence upon the area of the aperture 60. An area of the generally square aperture 60 shown in FIG. 4 is suitably characterized by a linear side dimension of the aperture 60. Table I shows exemplary values of the minimum capacitance $C_{min}$ and the maximum capacitance $C_{max}$ for the described light-sensitive metal-oxide-semiconductor with the p$^+$/p-doped silicon structure 50, 52 and having various linear side dimension lengths of the aperture 60.

TABLE I

| Capacitance values | | |
|---|---|---|
| Linear aperture side dimension length of a square aperture | Minimum capacitance $C_{min}$ | Maximum capacitance $C_{max}$ |
| 20 microns | 0.07 pF | 0.8 pF |
| 50 microns | 0.45 pF | 5 pF |
| 100 microns | 1.75 pF | 20 pF |
| 200 microns | 7 pF | 80 pF |
| 250 microns | 17.5 pF | 125 pF |

Preferably, the tuned resonant frequency at which the resonant circuit is visible in magnetic resonance images corresponds to a capacitance that is intermediate between the minimum capacitance $C_{min}$ and the maximum capacitance $C_{max}$. In this arrangement, the tuned resonant frequency can be precisely adjusted to correspond to the magnetic resonance frequency measured by the magnetic resonance imaging scanner 16 by making suitable precise adjustments to the illumination intensity $I_{light}$. Moreover, designing the resonant circuit 22 so that an intermediate capacitance provides the tuned resonance frequency allows the tuned resonance frequency to be adjusted upward or downward to accommodate, for example, a magnetic resonance frequency shift introduced by a different magnetic field applied by the magnetic resonance imaging scanner 16. However, it is also contemplated to design the tip tracking device 20 such that the minimum capacitance $C_{min}$ corresponds to the tuned resonance frequency for visibility, or to design the tip tracking device 20 such that the maximum capacitance $C_{max}$ corresponds to the tuned resonance frequency for visibility.

The described light sensitive metal-insulator-semiconductor capacitor is exemplary only. Those skilled in the art can construct other light sensitive metal-insulator-semiconductor capacitors having capacitance characteristics that are suitable for specific applications. For example, one or both oxide layers 54, 56 can be replaced by a silicon oxynitride layer, a silicon nitride layer, or the like deposited by plasma deposition or another deposition technique. Similarly, an n$^+$/n doped semiconductor structure can be substituted for the p$^+$/p doped semiconductor structure 50, 52. Moreover, a group III-group V compound semiconductor-based light sensitive metal-insulator-semiconductor capacitor such as a gallium arsenide-based light sensitive metal-insulator-semiconductor capacitor can be substituted for the described silicon-based light sensitive metal-oxide-semiconductor capacitor.

For the exemplary silicon-based light sensitive metal-oxide-semiconductor capacitor, the light source 40 is suitably a light emitting diode or a laser emitting in the visible or near infrared. In one preferred embodiment, a laser diode outputting light in a wavelength range between about 650 nm and 900 nm is suitably used. If a light sensitive metal-insulator-semiconductor capacitor includes a semiconductor material with a larger band gap than silicon, a shorter wavelength light source outputting light at a wavelength greater than the bandgap of the semiconductor material is preferably employed.

With returning reference to FIG. 1 and with further reference to FIG. 6, one suitable embodiment of the tip tracking device 20 at the tip 14 of the catheter 10 is described. In the embodiment of FIG. 6, the light sensitive metal-insulator-semiconductor capacitor 30 is bonded directly to the tip 14 of the catheter 10. The inductive coil 32 is also bonded to the tip 14 of the catheter 10. The discrete components 30, 32 can be bonded using a transparent epoxy, an acrylic bonding material, or the like. Preferably, the tip tracking device 20 is encapsulated by a shrink sleeve 70, an encapsulating epoxy, a potting material, or the like to hermetically seal and electrically insulate the tip tracking device 20.

Preferably, a size of the tip tracking device 20 is sufficiently small so that the tip tracking device 20 appears as a single point at the resolution of the reconstructed magnetic resonance images. Typically, the catheter 10 has a diameter of about 2 mm or less. In one embodiment, for example, the catheter has an outer diameter of 1.6 mm. A length of the tip tracking device 20 is preferably less than a thickness $d_{slice}$ of the imaging slice. Typically, the slice thickness $d_{slice}$ is between about 6 mm and about 10 mm for imaging performed during tip tracking. In one preferred embodiment, the tip tracking device 20 is about 3 mm long.

The embodiment of FIG. 6, in which the light sensitive metal-insulator-semiconductor capacitor 30 and the coil 32 are directly bonded to the tip 14 of the catheter 10, has certain disadvantages. There may be difficulties in bonding and electrically interconnecting the circuit components 30, 32 on the tip 14 of the elongated catheter 10. Moreover, this approach makes it difficult to replace the tip tracking device 20 if device fails or if the catheter 10 is deployed in conjunction with a different magnetic resonance scanner having a different main magnetic field strength. (Of course, depending on the illumination dependent capacitance range and corresponding range of selectable resonant frequencies, the LC circuit may be adapted for different scanners by adjusting the intensity of the illumination). Still further, the tip 14 of the catheter 10 may contain fragile or thermally sensitive components that could be damaged during the bonding and interconnection of the light sensitive metal-insulator-semiconductor capacitor 30 and the coil 32.

With reference to FIG. 7, another tip tracking device 20' is described. The tip tracking device 20' is a hybrid circuit formed on a hollow cylindrical insulating sleeve 74 made of plastic or another electrically insulating material. The light sensitive metal-insulator-semiconductor capacitor 30 is a discrete element as described previously herein, which is bonded to an outer surface of the hollow cylindrical insulating sleeve 74. The coil 32 is replaced by a plurality of electrically interconnected printed circuit coils 32' that are deposited onto the outer surface of the hollow cylindrical insulating sleeve 74. In one embodiment, several complete resonance circuits are deposited each including one metal-insulator-semiconductor capacitor 30 and a plurality of electrically interconnected printed circuit coils 32'. These capacitors 30 may be addressed by one optical fiber 36 or each circuit may be addressed by a separate fiber 36. The printed circuit coils 32' are preferably thin films of copper or another electrically conductive material formed on the cylindrical sleeve 74 using lithographic techniques commonly used to form electrical traces on printed circuit boards, planar microwave circuit layouts, and the like. The light sensitive metal-insulator-semiconductor capacitor 30 is electrically connected with the printed circuit coils 32' using suitable methods such as wire bonding or a combination of wire bonding to connect the contacting electrode 64 and direct surface bonding to connect the backside contacting electrode 66.

The hollow cylindrical insulating sleeve 74 defines the length of the hybrid circuit tip tracking device 20', and is preferably about 3 mm or less. In addition to keeping the hybrid circuit tip tracking device 20' close to or smaller than the imaging resolution, the cylindrical sleeve 74 should be kept short to reduce its effect on the flexibility of the catheter 10. The hollow cylindrical insulating sleeve 74 has an inner diameter sized to fit over the tip 14 of the catheter 10. The hollow cylindrical insulating sleeve 74 preferably is frictionally retained on the tip 14 of the catheter 10. A shrink-sleeve similar to the shrink-sleeve 70 of FIG. 6, an epoxy or acrylic encapsulant, or the like is preferably applied to hermetically seal at least the resonant circuit of the tip tracking device 20'. More preferably, the shrink sleeve or encapsulant additionally extends over and beyond the cylindrical sleeve 74 to secure or contribute to securing the tip tracking device 20' to the tip 14 of the catheter 10.

The use of the plurality of printed circuit coils 32' forming one or more resonant circuits arranged around the hollow cylindrical insulating sleeve 74 reduces directionality of the coupling strength of the resonant circuit with the radio frequency excitation pulse produced by the magnetic resonance imaging scanner 16, and reduces directionality of the radio frequency resonance signals output by the coils 32' in response to the excitation pulse. Moreover, the use of printed circuitry produces a low profile tip tracking device 20' which is advantageous for insertion into the subject 12. Optionally, the $p^+$ silicon substrate 50 of the light sensitive metal-insulator-semiconductor capacitor 30 is thinned prior to bonding of the light sensitive metal-insulator-semiconductor capacitor 30 to the cylindrical sleeve 74 to reduce the outward projection of the light sensitive metal-insulator-semiconductor capacitor 30 away from the cylindrical sleeve 74. The profile of the tip tracking device 20' is also optionally reduced by running the optical fiber 36 parallel to the sleeve 74 and providing side optical coupling, for example by coupling the optical fiber 36 to the light sensitive metal-insulator-semiconductor capacitor 30 using a fiber tip cleaved at a 45° angle to redirect light sideways into to aperture 60 of the light-sensitive metal-insulator-semiconductor capacitor 30.

While the plurality of electrically interconnected printed circuit coils 32' is shown in FIG. 7 as being deposited on the sleeve 74, it is also contemplated to deposit printed circuit coils directly onto a surface at the tip 14 of the catheter 10 to form printed circuit coils directly on the tip 14 of the catheter 10. In this way, the hybrid resonant circuit can be disposed directly onto the tip 14 of the catheter 10 rather than on the sleeve 74.

With returning reference to FIG. 1, during insertion of the catheter 10, the magnetic resonance imaging scanner 16 preferably rapidly repeats a fast scanning sequence that shows the position of the tip 14 within the subject 12. For this purpose, three-dimensional volumetric imaging by acquisition of imaging data for a succession of adjacent image slices may be too slow to provide effective real-time tip tracking. In one preferred embodiment, the tip tracking is performed as follows. The volume of interest is first excited in a non-spatially selective manner. This can be accomplished, for instance, by applying a radio frequency excitation pulse without a slice-select gradient or with a wide slab or slice select pulse. A magnetic field gradient is then applied along a projection direction perpendicular to the slice direction during magnetic resonance readout to acquire projection data The magnetic field gradient applied during magnetic resonance readout is preferably along the z-direction in FIG. 1. In this manner, a one-dimensional projection is generated perpendicular to the slices.

With reference to FIG. 8, projection data acquired using the above method is diagrammatically shown. A background signal 80 corresponds to an intensity of magnetic resonance from the subject 12 at each spatial position along the projection. For an axially directed projection, each spatial position of the projection corresponds to an axial slice. In the spatial position corresponding to the axial slice 24 shown in FIG. 1 that contains the tip tracking device 20, a slightly larger or enhanced magnetic resonance projection signal 82 is observed due to additional the resonance signal output by the tip tracking device 20. Based on the signal 82 the slice containing the tip tracking device 20 is identified. Preferably, a slice imaging sequence is then applied using a slice-selective magnetic field gradient to select the slice 24 for imaging. The reconstructed image of the slice 24 includes an image of the tip tracking device 20, so that the tip tracking device 20 is localized in three-dimensional space. Optionally, a few adjacent slices, such as adjacent slice on either side of the selected slice 24, are also imaged to provide a thin volume image. This tracking sequence including the projection measurement and single- or multi-slice imaging is repetitively performed to provide real-time tracking of the tip 14 of the catheter 10. Alternatively, two dimensional projection images along the x- and y-axes can be generated, rather than a one-dimensional projection. The projection images along the x- and y-axes give the x, y, and z coordinates of the tracking device, enabling the tracking device to be detuned during imaging to avoid artifacting the diagnostic images. Preferably, a marker is superimposed on the diagnostic image at the location determined from the projection images.

In some instances, the enhanced signal 82 is close to the background signal 80. In one approach, the background signal is substantially removed. Two projection measurements are performed in rapid succession, one performed with the tip tracking device 20 tuned to the tuned resonant frequency in which the tip is visible in the magnetic resonance image and the other performed with the tip detuned and hence substantially invisible. The two projections are subtractively combined to substantially remove the background signal 80, leaving the enhanced signal 82. The successive imaging approach, however, can be susceptible to blurring if the subject 12 moves or if the state of the magnetization changes between the two successive projection measurements.

In an improved background removal approach which is less sensitive to motion blurring, a single projection is acquired. During readout acquisition of the projection k-space data, the light source 40 is modulated to modulate the resonance frequency of the tip tracking device 20 between the visible state and the invisible state. Preferably, k-space is two-fold oversampled and the tracking device visible and invisible data points are collected alternately. For reconstruction, the k-space data points belonging to either state are separately Fourier transformed into the spatial domain and subtractively combined to substantially remove the noise signal at that spatial position. In this manner, the temporal separation between the subtractively combined tuned and detuned projection measurements at each spatial position is reduced to a switching time between the tuned (visible) and detuned (invisible) states. Advantageously, the tip tracking device 20 including the light sensitive metal-insulator-semiconductor capacitor 30 can be cycled between the visible and invisible states at a cycle period of between about 2 microseconds and about 4 microseconds, which is fast enough to substantially eliminate motion blurring or other sources of undesired differences.

While the various tip tracking processes have been described with reference to the tip tracking device 20, they are also suitably implemented using the hybrid circuit tip tracking device 20' or another tip tracking device employing one or more metal-insulator-semiconductor capacitor elements. Indeed, the hybrid circuit tip tracking device 20' is suitably substituted for the tip tracking device 20 in the interventional system of FIG. 1 for performing an interventional procedure on the subject 12 while being monitored by the magnetic resonance imaging scanner 16. Moreover, while the tip tracking devices 20, 20' have been described as being positioned at the tip 14 of the catheter 10, it is also contemplated to arrange one or more tracking devices such as the tracking devices 20, 20' at other positions along the catheter 10 to provide coordinates of points along the catheter.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. An interventional instrument for use in an interventional procedure performed on an associated subject and monitored by magnetic resonance imaging, the interventional instrument including:
    an element adapted for insertion into the associated subject for performing the interventional procedure;
    an optical fiber arranged to deliver light to a selected location on the element; and
    a resonant circuit disposed at the selected position on the element, the resonant circuit including a coil having a coil inductance and a light-sensitive metal-insulator-semiconductor capacitor optically coupled with the optical fiber and having a selectable capacitance determined by an intensity of light delivered thereto by the optical fiber, a selected resonance frequency of the resonant circuit being determined by the coil inductance and the selected capacitance, the selected resonance frequency being selectable by adjusting the light intensity to correspond to a tuned resonance frequency detected by the magnetic resonance imaging.

2. The interventional instrument as set forth in claim 1, wherein the resonant circuit is an LC circuit having an inductance corresponding to the coil inductance and a capacitance corresponding to the selected capacitance, and the selected resonance frequency of the resonant circuit is proportional to an inverse of a square-root of a product of the inductance and the capacitance.

3. The interventional instrument as set forth in claim 1, further including:
    a sleeve on which the resonant circuit is disposed, the sleeve being arranged over a tip of the element.

4. The interventional instrument as set forth in claim 1, further including:
    a shrink-sleeve disposed over the resonant circuit, the shrink-sleeve hermetically sealing the resonant circuit.

5. The interventional instrument as set forth in claim 1, wherein the resonant circuit is a hybrid circuit including:
    a printed circuit embodying the coil; and
    a discrete semiconductor device embodying the light-sensitive metal-insulator-semiconductor capacitor, the discrete semiconductor device being electrically coupled with the printed circuit.

6. The interventional instrument as set forth in claim 1, further including:
    one or more additional resonant circuits disposed at other selected positions on the element.

7. The interventional instrument as set forth in claim 1, wherein the light-sensitive metal-insulator-semiconductor capacitor is a silicon-based metal-oxide-semiconductor device.

8. The interventional instrument as set forth in claim 1, wherein the light-sensitive metal-insulator-semiconductor capacitor includes:

one of an n-n+ doped semiconductor layer structure and a p-p+ doped semiconductor layer structure configured to maximize a quality factor of the resonant circuit at the tuned resonance frequency.

9. The interventional instrument as set forth in claim 1, wherein:
the element is tubular and flexible; and
the optical fiber is disposed inside of a lumen of the flexible tubular element.

10. The interventional instrument as set forth in claim 1, wherein the tuned resonance frequency corresponds to a light intensity delivered by the optical fiber that is intermediate between a minimum intensity and a maximum intensity that can be delivered by the optical fiber.

11. A system for performing an interventional procedure on an associated subject monitored by magnetic resonance imaging, the system including:
a magnetic resonance imaging scanner for performing the magnetic resonance imaging; and
an interventional instrument as set forth in claim 1.

12. The system as set forth in claim 11, further including:
a controller for controlling the system to perform a tracking process including:
exciting magnetic resonance in a three-dimensional volume containing the selected location on the element;
acquiring magnetic resonance data along a projection perpendicular to an imaging slice;
during acquisition of magnetic resonance data, modulating the intensity of light delivered by the optical fiber to modulate the selected resonance frequency between the tuned resonance frequency and a detuned resonance frequency not detected by the magnetic resonance imaging scanner; and
processing the magnetic resonance data to produce projection data substantially indicative of a magnetic resonance signal produced by the resonant circuit.

13. A method for manufacturing an interventional instrument as set forth in claim 1, the method including one of:
sliding a sleeve over the selected location on the element, the resonant circuit being disposed on the sleeve,
forming a lithographically patterned film defining the coil on a sleeve, bonding the light-sensitive metal-insulator-semiconductor capacitor to the sleeve, electrically connecting the lithographically patterned film and the light-sensitive metal-insulator-semiconductor capacitor to define the resonant circuit, and sliding the sleeve over the selected location on the element, the resonant circuit being disposed on the sleeve, and
bonding a discrete inductive element defining the coil to the selected location on the element, bonding the light-sensitive metal-insulator-semiconductor capacitor to the selected location on the element, and electrically connecting the discrete inductive element and the light-sensitive metal-insulator-semiconductor capacitor to define the resonant circuit.

14. An interventional instrument for use in an interventional procedure performed on an associated subject and monitored by magnetic resonance imaging, the interventional instrument including:
an element adapted for insertion into the associated subject for performing the interventional procedure;
an optical fiber arranged to deliver light to a selected location on the element; and
a resonant circuit disposed at the selected position on the element, the resonant circuit including a coil having a coil inductance and a light-sensitive metal-insulator-semiconductor capacitor optically coupled with the optical fiber and having a selectable capacitance determined by an intensity of light delivered thereto by the optical fiber, a selected resonance frequency of the resonant circuit being determined by the coil inductance and the selected capacitance, the selected resonance frequency being selectable by adjusting the light intensity to correspond to a tuned resonance frequency detected by the magnetic resonance imaging, the light-sensitive metal-insulator-semiconductor capacitor including:
a heavily doped semiconductor substrate,
a more lightly doped semiconductor layer disposed over the heavily doped semiconductor substrate,
an insulator layer disposed over the more lightly doped semiconductor layer, and
a conductive layer disposed over the insulator layer.

15. The interventional instrument as set forth in claim 14, wherein a doping of the more lightly doped semiconductor layer is selected such that a depth of a space charge region in the more lightly doped semiconductor layer at zero potential substantially coincides with a thickness of the more lightly doped semiconductor layer.

16. A method of using an interventional instrument which includes an element adapted for insertion into the associated subject for performing the interventional procedure; an optical fiber arranged to deliver light to a selected location on the element; and a resonant circuit disposed at the selected position on the element, the resonant circuit including a coil having a coil inductance and a light-sensitive metal-insulator-semiconductor capacitor optically coupled with the optical fiber and having a selectable capacitance determined by an intensity of light delivered thereto by the optical fiber, a selected resonance frequency of the resonant circuit being determined by the coil inductance and the selected capacitance, the selected resonance frequency being selectable by adjusting the light intensity to correspond to a tuned resonance frequency detected by the magnetic resonance imaging, the method including:
exciting magnetic resonance in a volume containing the selected location on the element;
acquiring k-space data;
for the acquiring of k-space data, intensity-modulating the intensity of light delivered to the light-sensitive metal-insulator-semiconductor capacitor to modulate the selected resonance frequency between the tuned resonance frequency and a detuned resonance frequency not detected by the magnetic resonance imaging;
Fourier transforming k-space data acquired with the selected resonance frequency tuned to the tuned resonance frequency into a first spatial data set;
Fourier transforming k-space data acquired with the selected resonance frequency detuned into a second spatial data set; and
subtractively combining the first and second spatial data sets to produce a subtractively combined data set.

17. An intravascular imaging method performed using an interventional instrument which includes an element adapted for insertion into the associated subject for performing the interventional procedure; an optical fiber arranged to deliver light to a selected location on the element; and a resonant circuit disposed at the selected position on the element, the resonant circuit including a coil having a coil inductance and a light-sensitive metal-insulator-semiconductor capacitor optically coupled with the optical fiber and having a selectable capacitance determined by an intensity of light delivered thereto by the optical fiber, a selected resonance frequency of the resonant circuit being determined by the coil inductance and the selected capacitance, the selected resonance frequency being selectable by adjusting the light intensity to correspond to a tuned resonance frequency detected by the magnetic resonance imaging, the intravascular imaging method including:

inserting at least a portion of the element including the selected location into the associated subject;

acquiring magnetic resonance tracking data with the element inserted into the associated subject and with the intensity of light delivered to the light-sensitive metal-insulator-semiconductor capacitor selecting the tuned resonance frequency;

determining position coordinates of the selected location on the element in the associated subject based on the magnetic resonance tracking data;

acquiring intravascular magnetic resonance imaging data of a region including the determined position coordinates with the element inserted into the associated subject and with the intensity of light delivered to the light-sensitive metal-insulator-semiconductor capacitor selecting a detuned resonance frequency not detected by the magnetic resonance imaging; and reconstructing the intravascular magnetic resonance imaging data to form a reconstructed image.

18. An apparatus comprising:

a catheter including an optical fiber arranged to deliver light to a tip of the catheter, the catheter further including a resonant circuit disposed at the tip of the catheter, the resonant circuit including a coil and a light-sensitive metal-insulator-semiconductor capacitor, the optical fiber being arranged to deliver light to the light-sensitive metal-insulator-semiconductor capacitor to adjust a capacitance of the light-sensitive metal-insulator-semiconductor capacitor.

19. The apparatus as set forth in claim 18, further including:

a shrink-sleeve disposed over the resonant circuit, the shrink-sleeve hermetically sealing the resonant circuit.

20. The apparatus as set forth in claim 18, wherein the light-sensitive metal-insulator-semiconductor capacitor comprises:

a silicon-based metal-oxide-semiconductor (MOS) capacitor.

* * * * *